US008349140B2

(12) United States Patent
Cereceda Balic et al.

(10) Patent No.: US 8,349,140 B2
(45) Date of Patent: Jan. 8, 2013

(54) DEVICE FOR EXTRACTION OF ORGANIC CHEMICAL COMPOUNDS WITH TOXIC PROPERTIES, WHICH ARE PRESENT IN ATMOSPHERIC SAMPLES, BY USING SOLVENTS HEATED BY THE APPLICATION OF FOCALIZED MICROWAVES IN OPEN SYSTEMS (NOT PRESSURIZED)

(76) Inventors: Francisco Cereceda Balic, Quilpue (CL); Hector Carrasco Espinosa, Vina del Mar (CL); Manuel Olivares Salinas, Vina del Mar (CL); Gabriel Cereceda Balic, Quilpue (CL)

( * ) Notice: Subject to any disclaimer, the term of this patent is extended or adjusted under 35 U.S.C. 154(b) by 985 days.

(21) Appl. No.: 12/293,129

(22) PCT Filed: Mar. 15, 2007

(86) PCT No.: PCT/ES2007/070056

§ 371 (c)(1),
(2), (4) Date: Sep. 16, 2008

(87) PCT Pub. No.: WO2007/104823

PCT Pub. Date: Sep. 20, 2007

(65) Prior Publication Data

US 2009/0038931 A1 Feb. 12, 2009

(30) Foreign Application Priority Data

Mar. 16, 2006 (CL) .................................... 589-2006

(51) Int. Cl.
*B01D 11/00* (2006.01)

(52) U.S. Cl. ........................... 203/39; 202/170; 202/234

(58) Field of Classification Search .................... 203/39, 203/100; 202/170, 234; 210/748.01, 748.07; 333/81 R, 81 A, 81 B, 176, 202, 206; 422/21; 219/678, 690

See application file for complete search history.

(56) References Cited

U.S. PATENT DOCUMENTS

| | | | | |
|---|---|---|---|---|
| 3,309,634 | A * | 3/1967 | Wheeler et al. | 333/81 R |
| 3,845,422 | A * | 10/1974 | Rhodes | 333/208 |
| 4,028,651 | A * | 6/1977 | Leetmaa | 333/212 |
| 4,894,592 | A * | 1/1990 | Ervin et al. | 315/248 |
| 5,796,080 | A * | 8/1998 | Jennings et al. | 219/697 |
| 5,972,711 | A * | 10/1999 | Barclay et al. | 436/55 |
| 6,258,329 | B1 * | 7/2001 | Mutterer et al. | 422/186.29 |
| 6,288,379 | B1 * | 9/2001 | Greene et al. | 219/702 |
| 6,303,005 | B1 * | 10/2001 | Lautenschlager | 202/160 |
| 2008/0001686 | A1 * | 1/2008 | Chao et al. | 333/254 |

OTHER PUBLICATIONS

Leeson, D.B. "Microwave Filters" 1999, accessed Aug. 4, 2011 at: <http://home.sandiego.edu/~ekim/e194rfs01/filterek.pdf>.*

Basheer, C., Obbard, J., Lee, H., "Analysis of persistent organic pollutants in marine sediments using a novel microwave assisted solvent extraction and liquid-phase microextraction technique". Journal of Chromatography, vol. 1068, pp. 221-228, Elsevier (c) 2005.*

Hermann, Christine, "First Day in Organic Chemistry", Journal of Chemical Education, vol. 73 No. 9, pp. 852-854, American Chemical Society (c) 1996.*

* cited by examiner

*Primary Examiner* — Robert A Hopkins
(74) *Attorney, Agent, or Firm* — Karim Lagobi

(57) ABSTRACT

Device to extract organic chemical compounds from particulate material (MP) that comes from atmospheric samples, using solvents heated by the application of focalized microwaves (MW), performed in open systems, which consists of:
- a magnetron;
- an electronic control circuit of the magnetron;
- a distillation flask that holds the solvent with the sample to be heated;
- a filter for blocking microwaves, which allows getting out the vapor produced by the ebullition of the solvent with the sample to reach a reflux medium that allows condensing that vapor; and
- a waveguide connected at one extreme with the magnetron and electronic control circuit, and at the other extreme with the distillation flask to be heated, the microwave blocking filter and the reflux medium.

13 Claims, 6 Drawing Sheets

DEVICE FOR EXTRACTION OF ORGANIC CHEMICAL COMPOUNDS WITH TOXIC PROPERTIES, WHICH ARE PRESENT IN ATMOSPHERIC SAMPLES, BY USING SOLVENTS HEATED BY THE APPLICATION OF FOCALIZED MICROWAVES IN OPEN SYSTEMS (NOT PRESSURIZED)

FIELD OF THE INVENTION

The invention describes a device for extraction of organic chemical compounds with toxic properties such as Polycyclic Aromatic Hydrocarbons (PAHs) and Polychlorinated Biphenyls (PCBs), contaminants present in particulate matter of atmospheric samples, which is carried out using solvents that have been heated by means of focalized microwaves (MW), performed in open systems (not pressurized).

BACKGROUND OF THE INVENTION

The employment of MW to extract organic compounds from particulate matter (PM) resulting from air samples has been mainly used in applications of focalized MW in closed systems, however, the high pressures and temperatures reached in this type of equipment compels the development of very sophisticated and expensive systems to achieve high safety standards. One possibility to simplify and reduce costs is to use MW in open systems. Major problems in these types of applications include an inability achieve a good absorption of electromagnetic energy by the organic solvents, the inability to regulate the electromagnetic power produced by the magnetron that generates the MW, and to limit MW radiation leaks, which can cause injury to those who operate these equipments.

Organic solvents are required for the extraction. Most of the appropriate solvents for this purpose (e.g. hexane, toluene and others) have apolar characteristics which makes them impossible to heat using MW.

In the market, there are two types of equipment for chemical extraction with MW, both of high cost, one pressurized and the other one open. In the open configuration, the device is designed for its employment in the generation of specific chemical reactions (e.g. synthesis), where the high energies obtained by the MW are used. In this way, these devices have a very limited capacity for manipulation of the equipment and glass material of traditional and standard use in a laboratory. Furthermore, the requirements for blocking MW leakage restricts the transition zone of these components from the focalized MW zone to the exterior. This problem necessitates the use of glass material specially designed for this purpose or the restriction of typical chemical procedures, such as reflux.

The trouble with the open configuration of MW equipment is the possibility of excessive MW leaks, which can be controlled by limiting the size and shape of the orifices present in the metallic structures that guide and focus the MW in the direction of the container that holds the sample to be heated and extracted, and in the transition zone of the laboratory glass material from the focalized MW zone to the exterior.

U.S. Pat. No. 6,061,926 ("Controlled energy density microwave-assisted processes", from May 16, 2000, by: Pare J R Jocelyn, Belanger Jacqueline M R and Punt Monique M.) describes the same principle of heating by absorption of MW, but restricted to small volumes of chemical solvents and transition zones, due to the need of limiting MW radiation leaks. This equipment is designed to carry out specific chemical reactions, such as synthesis of chemical compounds.

Consequently, there is a need for equipment that could address those problems of restriction of heating by MW, rapidity, efficiency, volume, safety and use of standard chemical laboratory material.

SUMMARY OF THE INVENTION

The objective of the invention is to develop a device for rapid, efficient and secure chemical extraction, using solvents heated by the application of focalized microwaves in open systems (not pressurized). This extraction device is designed to be used in the extraction of organic chemical compounds with toxic properties, such as HAPs and PCBs, which are contaminants present in atmospheric samples.

The invention is designed to heat polar solvents like water. When apolar solvents (e.g. hexane, toluene and others) are used, like those typically utilized in the extraction of samples containing organic contaminants, it is necessary to add an amount of a polar solvent to the sample (e.g. acetone, isopropyl alcohol and others). The polar solvent absorbs the MW that inundate the sample and as a consequence rapidly and efficiently heats the apolar solvent (e.g. toluene) until ebullition. The choice and proportion of polar solvent are determined in such a way that when the sample is exposed to an oscillating electromagnetic field, the polar solvent absorbs as much energy as possible. Heating occurs as a result of molecular friction as the molecules rotate to align themselves with the oscillating electromagnetic field.

Another relevant aspect of this invention is a novel filter designed to block MW radiate that leaks to the exterior. This provides an important increase of the transition zone from where the focalized MW (interior of the equipment) are generated to the place where the glass material is typically used in the laboratory (exterior of the equipment). The increased transition zone improves the extraction capacity, thereby allowing the utilization and connection of equipment and glass material of traditional and standard use in the laboratory. At the same time, it allows for the extraction using a larger volume of solvent by taking advantage of the efficiency and rapidity of heating using focalized MW. This filter for blocking MW radiation leaks constitutes a characteristic that has not been found in the state of the art.

The working principle of the equipment is based on heating of substances, solvents in this case, due to the friction produced in the polar molecules, that is to say it is a mechanical effect induced by the oscillation of the electromagnetic field generated and canalized to the interior of the MW subsystem. The MW energy is generated by a magnetron, and it is then canalized by a waveguide to the glass container that holds the solvent. The waveguide and its termination are designed to achieve optimal MW absorption by the sample and produce minimal reflection towards the magnetron. The filter blocks the energy delivered by the magnetron such that it does not escape (or very little escapes) to the exterior and, combined with the waveguide, directs the energy towards the sample such that the energy is efficiently absorbed by the sample. Power regulation is also an important aspect because it is required to maintain a condition of constant and moderate ebullition. This is accomplished by means of an electronic control programmed such that it initially provides 100% power to quickly reach the ebullition state, and then reduces the power to approximately 60% of work cycle and preferably an approximate cadency of 1 Hz to maintain and regulate the process.

The equipment works at a frequency band of 2.450 MHz, using a magnetron of the type commonly found in domestic microwave ovens. The magnetron is disposed in a waveguide such that the container that holds the extraction solvent absorbs the maximum MW energy, where the power is controlled by means of the electronic control.

The developed equipment uses a magnetron of the type widely used in domestic MW ovens, which translates into a product of moderate and very competitive cost compared to other market alternatives.

In summary, the objectives of the invention are to provide an equipment for rapid and efficient chemical extraction, using solvents heated by the regular application of electronically focalized MW performed in non-pressurized, open systems, with a magnetron of the type widely used in domestic MW ovens of low cost, and incorporating a filter for blocking MW from exiting, thereby allowing for the use of standard laboratory elements of much major capacity and similar equipments.

DESCRIPTION OF THE PREFERRED EMBODIMENTS

Figure 1:
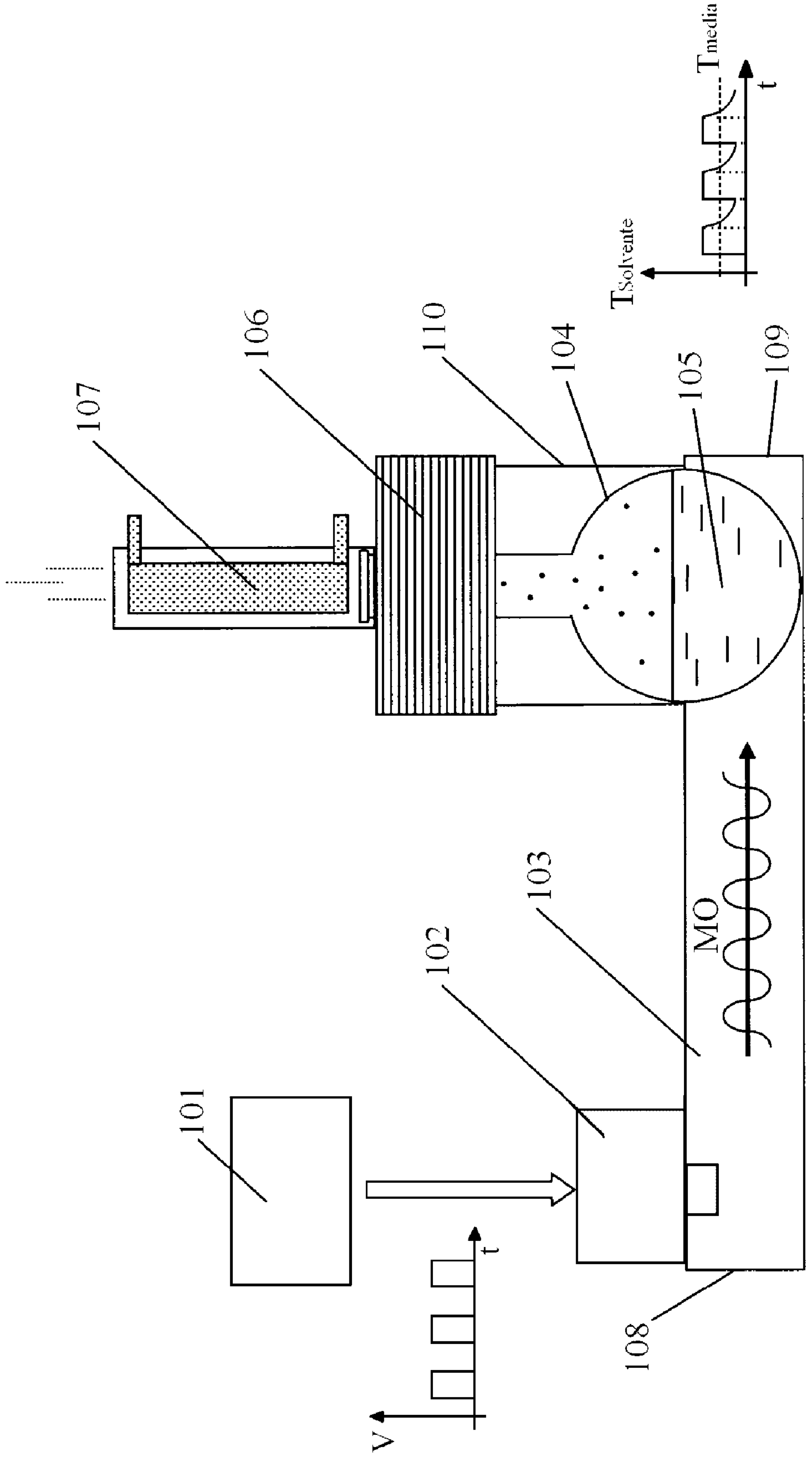
FIG. 1 shows a general, complete and functional scheme of the proposed invention.

The developed equipment works at the frequency band of 2,450 MHz, using a magnetron of the type widely used in domestic MW ovens of low cost, disposed in a waveguide. The waveguide is designed such that the container that holds the extraction solvent absorbs the maximum MW energy, where the power provided by the magnetron is programmed and controlled by a specifically designed electronic circuit. The scheme of FIG. 1 shows the execution of the invention in a simple and functional form. The magnetron (102) generates the MW signal whose power is regulated by the electronic circuit (101). The microwaves are guided by the waveguide (103) to the standard glass container for the solvent (104), which for example could be a round bottom distillation flask with 250 ml capacity that holds the solvent to be heated (105) (extraction solvent). The vapor produced by the ebullition of the solvent ascends through the neck of the flask to the condenser of the reflux medium (107) and comes out from the interior of the MW equipment to the exterior through the filter for blocking the MW (106). The solvent in vapor phase is typically condensed in the reflux medium (107) and goes back to the distillation flask (104) to initiate a new reflux cycle.

Controlling the output power is achieved by varying the work cycle in an on/off feeding mode of the magnetron (102), but at substantially higher frequency (one cycle per second approximately) than the one used in the application of domestic ovens, because it requires an acceptable stable temperature of the substances to be heated, whose mass is considerably smaller in this application compared to the typical mass heated in domestic ovens. The regulation of power is initially at 100% to rapidly achieve ebullition, and then a work cycle close to 60% is used to keep the process regulated.

The waveguide (103) is designed according to the standard frequency of work specified in the literature, and its terminations (108 and 109) in the same manner, in order to achieve an optimal efficiency of transmission power among the magnetron (102), waveguide (103), and distillation flask (104).

Figure 2:
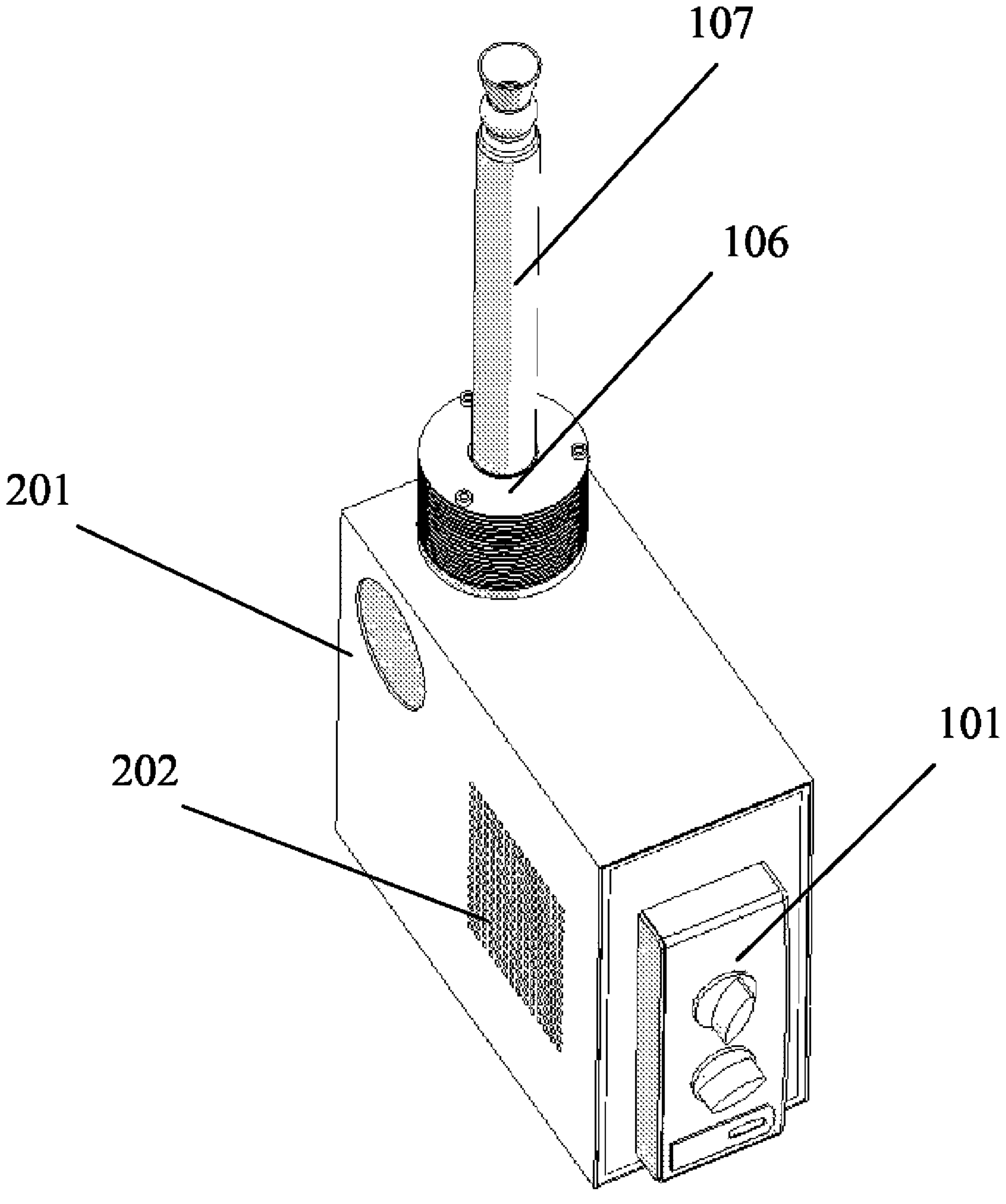
FIG. 2 shows a perspective view of the exterior of the whole equipment.
Figure 3:
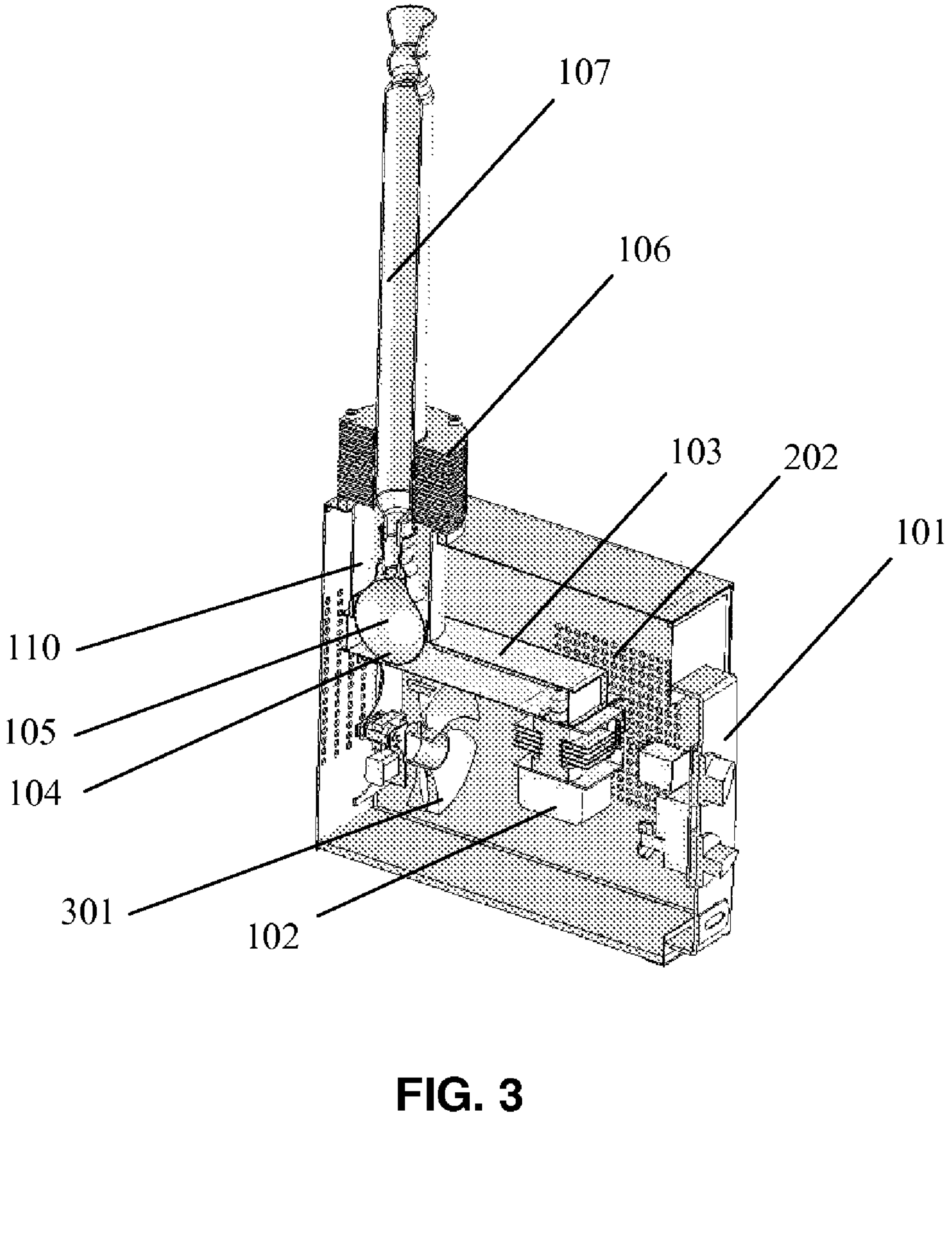
FIG. 3 shows a cut through perspective view of the interior of the equipment.
Figure 4:
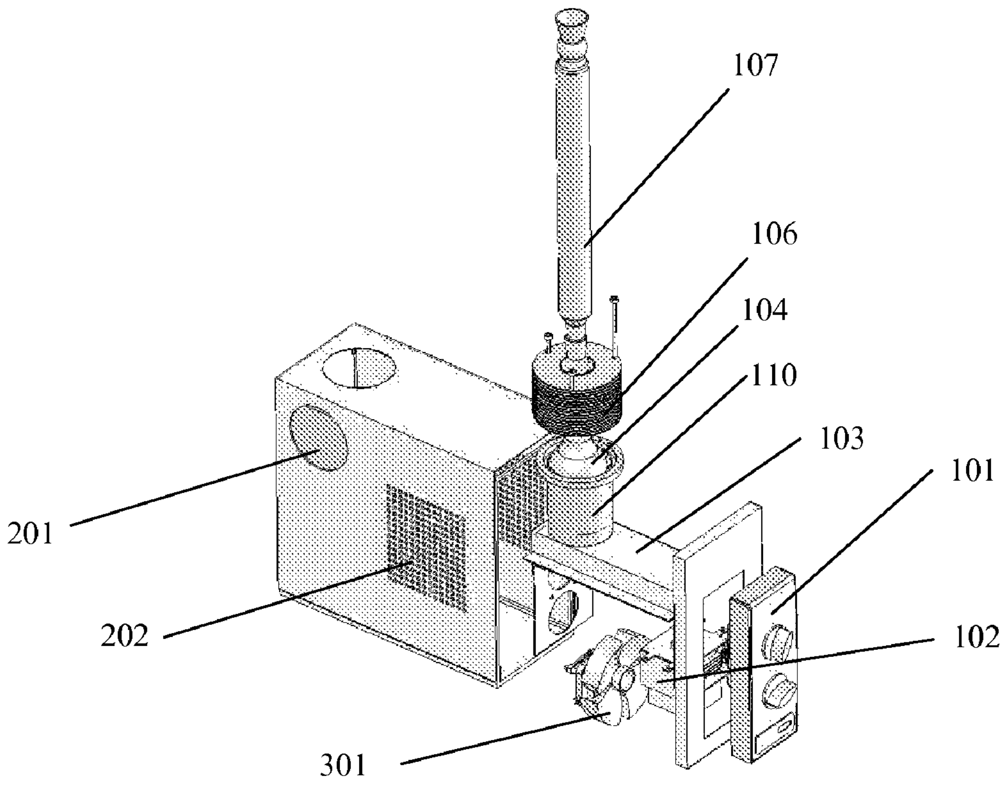
FIG. 4 shows a complete perspective view of the equipment and the interior components.
Figure 5:
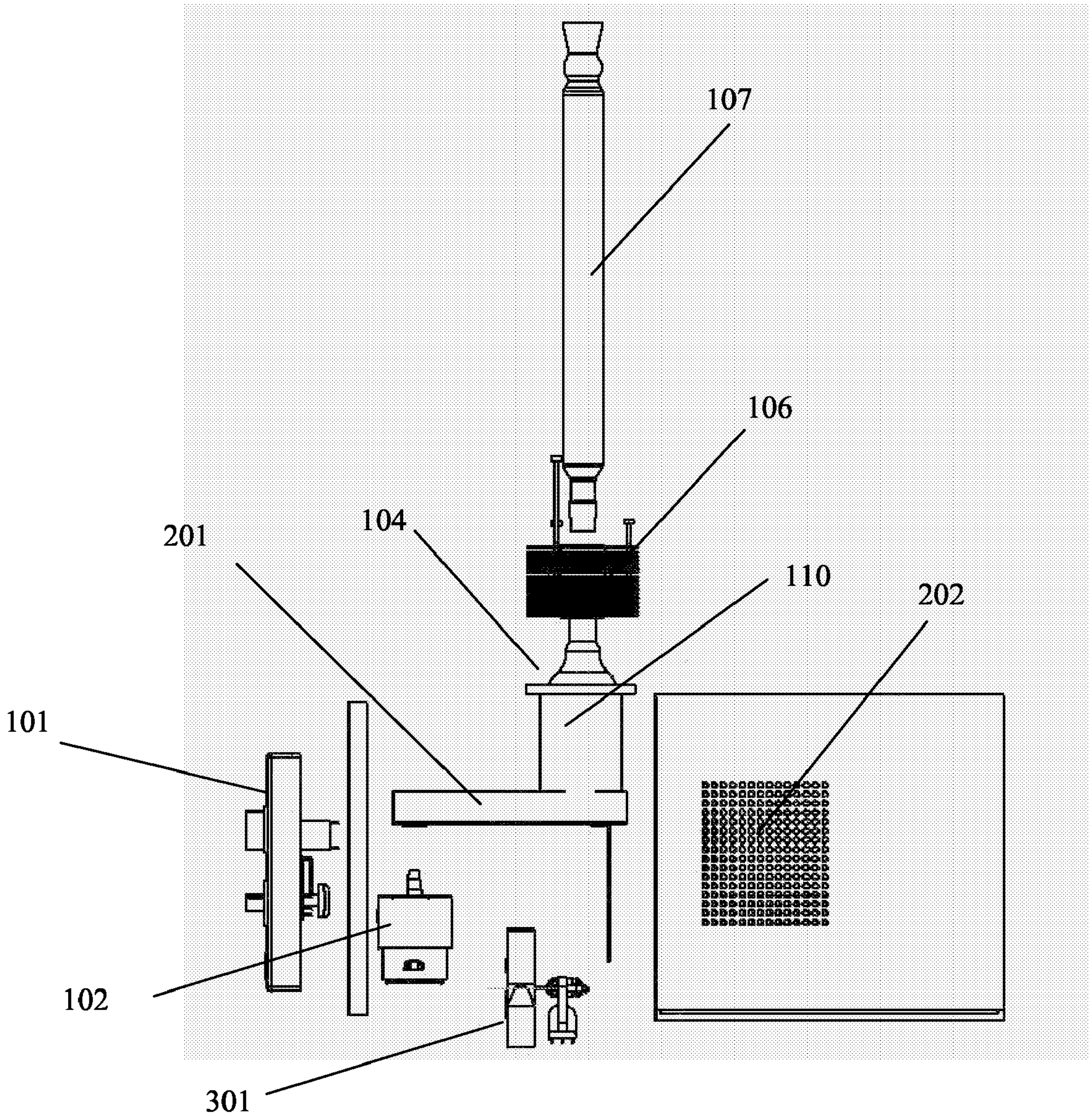
FIG. 5 shows a lateral view of a detailed breakdown of all the component parts of the equipment.

The distillation flask (104) (e.g. a typical standard 250 ml round bottom flask) is disposed in the waveguide (103) termination, in such a way that almost all the solvent to be heated (105) is located inside the waveguide (103), and it behaves as an absorbent load. The distillation flask (104) is introduced in the waveguide (103) through a conductor mesh cylinder (110), which acts as an electromagnetic shield, but at the same time it allows visualizing the process from the exterior of the equipment through another window shielded with the conductor mesh (201) that is shown in FIGS. 2, 3, and 4. The exterior diameter of the distillation flask (104) that holds the solvent, is equal to the interior width of the waveguide (103) and to the interior diameter of the conductor mesh cylinder (110), in such a form that the solvent covers a maximum of the transversal section of the waveguide (103) to achieve maximum efficiency of heating, as is shown in FIG. 1.

One of the key parts of the current invention is the safety device that reduces or prevents MW radiation leaks. The filter for blocking MW (106), which allows working with a standard distillation flask (104), a container with higher capacity than those used in the state of the art, and at the same time it constitutes a lid through which the distillation flask (104) is introduced into the conductor mesh cylinder (110) and waveguide (103) and taken out to the exterior of the MW equipment to load and unload solvent (105) in each process of extraction, as can be better appreciated in FIGS. 3 and 4. An external conductor mesh window (201) allows users to see the heating process from the outside through the conductor mesh cylinder (110).

Figure 6:
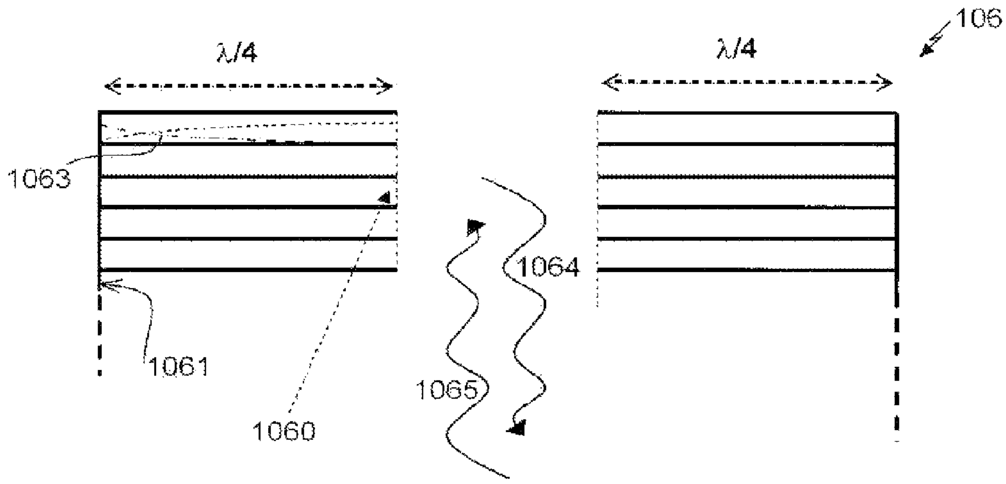
FIG. 6 shows a transverse cut view of the blocking filter for MW.

A detailed transverse cut view of the blocking filter for MW is shown in FIG. 6. The blocking filter for MW (106) is composed of a plurality of conductor plaques, or dishes, with cylindrical cavities or perforations through which passes the neck of the distillation flask (104). The circular conductor plaques have a thickness of 0.5 mm, with an exterior radius of 47 mm (1061) and an internal radius of 17 mm (1060), disposed in parallel form and separated by 2 mm, and all connected through the exterior in short circuit, and open in the interior perimeter (zone of the neck of the distillation flask (104)). Between the open interior perimeter and the closed exterior perimeter in short circuit, there is a distance of a quarter of a wavelength ($\lambda/4$) (30 mm) at the frequency of emission of the magnetron (102), in such a way that the perforations connected in short circuit in the exterior, transform into open circuits for the electromagnetic wave (1063) in the interior perimeter, where the neck of the distillation flask (104) passes, and as a consequence it reflects the MW (1065 and reflected 1064) before reaching the exterior. In FIGS. 2, 3 and 4, one can see the conductor plaques that form the cavities of the blocking filter for MW (106).

Figure 7:
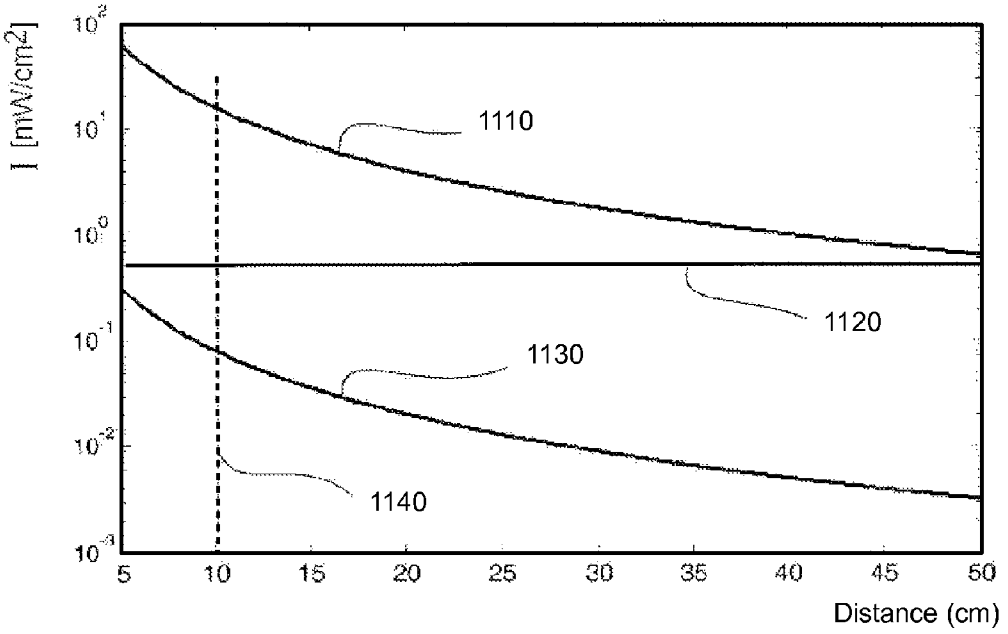
FIG. 7 shows measurement results and extrapolation of MW radiated intensity power, with and without the blocking filter.

FIG. 7 shows measurement results and extrapolation of MW intensity power radiated from the device, with and without the blocking filter. It is worth mentioning that excessive leaks of MW radiation, approximately greater than 0.5 mW/cm2, constitute a risk for the operator's health, according to Chilean legislation. The invention, incorporating the blocking filter for MW (106), which has been designed to practically prevents MW from exiting to the exterior, allows an experimental attenuation (1130) more than 20 dB in relation to not using the filter (1110). Considering the maximum power of MW available and needed in the magnetron (102) (approximately 800 W), this important reduction of MW radiation leaks to the exterior allows the equipment to work far below the threshold previously mentioned, a condition that is not met when the MW blocking filter (106) is not used. Without the filter, under the previous condition and for a typical distance no less than around 10 cm to the filter (1140), the radiation leaked to the exterior is around forty (40) times the maximum considered acceptable (1120). According to these measurements, radiated power (intersection of 1130 and 1140) of when using the filter is around ten times bellow the risk threshold (intersection of 1120 and 1140) for a typical work distance of 10 cm.

In regard to the velocity of solvent heating until reaching an ebullition condition, there have been obtained average times close to one minute in multiple essays, which are much shorter than those obtained with equipment for conventional heating by convection, those times being closer to minutes considering the same volume of solvent (e.g. toluene).

The fan (301) is used to counterbalance the inevitable heating of the magnetron (102), whose ventilation is accomplished through the metallic mesh window (202).

The invention claimed is:

1. A device for extracting organic chemical compounds from material in particle form atmospheric samples that uses solvents heated by the application of focalized microwaves in open systems comprising:

- a magnetron, where the magnetron has a frequency of emission;
- an electric control circuit of the magnetron;
- a distillation flask, where the distillation flask comprises a solvent with a sample to be heated;
- a microwave blocking filter, where the microwave blocking filter enables vapor produced by the ebullition of the solvent with the sample reaching a reflux medium to exit thereby causing the vapor produced by the distillation to condense;
- and a waveguide, which has in one end the magnetron and the electric control circuit, and in the other end the distillation flask to be heated, the microwave blocking filter and the reflux medium,
- wherein said microwave blocking filter is placed between said distillation flask and said reflux medium, and comprises a plurality of circular conductor plates, each with a central hole, in such a way that the plates constitute a cylindrical cavity in the microwave blocking filter's center through which the neck of the distillation flask is allowed to pass through, where said plates are disposed in parallel positions and connected in the exterior in short circuit, and where the distillation flask is open in the interior perimeter of the zone of the neck of the distillation flask;
- where between the open interior perimeter and the closed exterior perimeter in short circuit, there is a distance of a quarter of a wavelength (λ/4) at the frequency of emission of the magnetron, whereby the cylindrical cavities between the conductor plates ending in short circuit in the exterior transform into open circuits for an electromagnetic wave in the interior perimeter, and as a consequence, the electromagnetic wave rapidly attenuates and is blocked before reaching the exterior.

2. The device for extracting organic chemical compounds according to claim 1, wherein each circular conductor plate of the plurality of circular conductor plates has approximately 0.5 mm of thickness, with an exterior radius of approximately 47 mm and an internal radius of approximately 17 mm.

3. The device for extracting organic chemical compounds according to claim 2, wherein each circular conductor plates of the plurality of circular conductor plates disposed in parallel position are separated approximately by 2 mm between each other.

4. The device for extracting organic chemical compounds according to claim 1, where the magnetron comprises a power source, where the power source has a working cycle, wherein different power levels are achieved by varying the working cycle in on/off mode of the power source of the magnetron with a frequency of approximately one cycle per second.

5. The device for extracting organic chemical compounds according to claim 1, wherein the microwave blocking filter acts as a top of a conductor mesh cylinder which electromagnetically shields the exterior while at the same time allowing the process to be viewed from the exterior of the equipment through another window shielded with a conductor mesh, where the conductor mesh cylinder has an interior diameter, where the distillation flask has an exterior diameter, where the waveguide has an interior width, where the exterior diameter of the distillation flask is equal to the interior width of the waveguide as well as to the interior diameter of the conductor mesh cylinder whereby the solvent covers a maximum of a transversal section of the waveguide to achieve maximum efficiency of heating.

6. A device for extracting organic chemical compounds from atmospheric particles using solvents heated by the application of focalized microwaves in an open system comprising:

- a magnetron for emitting a microwave radiation having a radiation frequency, further comprising an electronic control circuit for controlling a working cycle of operation of said magnetron;
- a distillation flask positioned inside the device for receiving at least one polar solvent for heating with said microwave radiation;
- a waveguide for transmitting said microwave radiation from said magnetron to said distillation flask;
- a reflux medium connected to said distillation flask for allowing vapors to rise from said distillation flask, to condense in said reflux medium and to flow back into said distillation flask, wherein said reflux medium further configured for receiving atmospheric samples and allowing said vapors to mix with said atmospheric samples within said reflux medium; and
- a microwave blocking filter comprising a plurality of circular conductor plates disposed in parallel, wherein each plate having a central circular hole in such a way that said plurality of conductor plates when stacked in parallel form a cylindrical cavity at its center for allowing the neck of said distillation flask to connect with said reflux medium through said cylindrical cavity, wherein said plurality of circular conductor plates are connected at their external perimeter to short circuit said microwave radiation, and wherein the distance between the perimeter of said central cylindrical cavity and the external perimeter is a quarter of the wavelength (λ/4) at said radiation frequency.

7. The device of claim 6 further comprising each circular conductor plate of said plurality of circular conductor plates having a thickness of approximately 0.5 mm and an external radius of approximately 47 mm, and said central circular hole having a radius of approximately 17 mm.

8. The device of claim 7 further comprising each circular conductor plate of the plurality of circular conductor plates disposed in parallel position are separated approximately by 2 mm between each other.

9. The device of claim 6 further comprising a conductor mesh cylinder surrounding said distillation flask, for electromagnetically blocking said microwave radiation while allowing visual inspection of the distillation flask, said conductor mesh cylinder's first end connected to said microwave blocking filter and said conductor mesh cylinder's second end connected to one end of said waveguide, wherein said conductor mesh cylinder having an interior diameter equal to an interior diameter of said waveguide and exterior diameter of said distillation flask.

10. A device for extracting organic chemical compounds from atmospheric particles using solvents heated by the application of focalized microwaves in an open system comprising:

means for emitting a microwave radiation having a radiation frequency comprising a magnetron, further comprising means for electronically controlling a working cycle of operation of said magnetron;

means for receiving at least one polar solvent for heating with said microwave radiation comprising a distillation flask;

means for transmitting said microwave radiation from said means for emitting to said distillation flask;

means for condensing vapors produced by the heating of said polar solvent in said means for receiving said at least one polar solvent comprising a reflux medium, wherein said means for condensing is connected to said means for receiving said at least one polar solvent such that the condensate flows back into said for receiving said at least one polar solvent, wherein said means for condensing further configured for receiving atmospheric samples and allowing said vapors to mix with said atmospheric samples; and means for blocking microwaves comprising a plurality of circular conductor plates disposed in parallel, wherein each plate having a central circular hole in such a way that said plurality of conductor plates when stacked in parallel form a cylindrical cavity at its center for allowing glassware of said means for receiving said at least one polar solvent to connect with said means for condensing through said cylindrical cavity, wherein said plurality of circular conductor plates are connected at their external perimeter to short circuit said microwave radiation, and wherein the distance between the perimeter of said central cylindrical cavity and the external perimeter is a quarter of the wavelength ($\lambda/4$) at said radiation frequency.

11. The device of claim 10, wherein said plurality of circular conductor plates further comprising each circular conductor plate having a thickness of approximately 0.5 mm and an external radius of approximately 47 mm, and said central circular hole having a radius of approximately 17 mm.

12. The device of claim 11 further comprising each circular conductor plate of the plurality of circular conductor plates disposed in parallel position are separated approximately by 2 mm between each other.

13. The device of claim 10 further comprising means for electromagnetically blocking said microwave radiation while allowing visual inspection of the distillation flask, comprising a conductor mesh cylinder surrounding said means for receiving said at least one polar solvent, said conductor mesh cylinder's first end connected to said means for blocking microwaves and said conductor mesh cylinder's second end connected to one end of said means for transmitting, wherein said conductor mesh cylinder having an interior diameter equal to an interior diameter of said means for transmitting and an exterior diameter of said means for receiving said at least one polar solvent.

* * * * *